US00PP14664P39

(12) United States Plant Patent

Wilkinson et al.

(10) Patent No.: US PP14,664 P3

(45) Date of Patent: Apr. 6, 2004

(54) POPLAR NAMED 'SHINSEI'

(50) Latin Name: *Populus nigra×P. maximowiczii*
Varietal Denomination: Shinsei

(75) Inventors: Allan G Wilkinson, Palmerston North (NZ); Lindsay E Fung, Palmerston North (NZ)

(73) Assignee: The Horticulture and Food Research Institute of New Zealand Limited, Palmerston North (NZ)

( * ) Notice: Subject to any disclaimer, the term of this patent is extended or adjusted under 35 U.S.C. 154(b) by 25 days.

(21) Appl. No.: 10/159,949

(22) Filed: May 30, 2002

(65) Prior Publication Data

US 2003/0014792 P1 Jan. 16, 2003

(30) Foreign Application Priority Data

Jun. 25, 2001 (NZ) ..... POP006

(51) Int. Cl.[7] ..... A01H 5/00

(52) U.S. Cl. ..... Plt./218

(58) Field of Search ..... Plt./218

*Primary Examiner*—Bruce R. Campell
*Assistant Examiner*—A. Para
(74) *Attorney, Agent, or Firm*—Greenlee, Winner and Sullivan, P.C.

(57) ABSTRACT

A new and distinct poplar clonal cultivar, *Populus nigra* L.×*P. maximowiczii* A. Henry, is described. The cultivar results from a controlled pollination using a male *P. maximowiczii* from Hokkaido, Japan and a female *P. nigra* of unknown parentage. Both named parents are unpatented cultivars. The new cultivar is characterised by a narrow crown form, dark green foliage, high resistance to leaf rusts and anthracnose, and low palatability to possums.

5 Drawing Sheets

Genus and species of plant claimed: *Populus nigra×P. maximowiczii.*

CROSS REFERENCE TO RELATED APPLICATIONS

This application claims benefit of New Zealand PVR Application POP006, filed Jun. 25, 2001.

BACKGROUND OF THE INVENTION

The genus Populus consists of 30–40 named species many of which are able to hybridise with other species (within this genus). Poplars occur naturally throughout most parts of the temperate and cold regions of the Northern Hemisphere and have a long history of use by many societies in these areas.

A poplar breeding programme has been operating in New Zealand since 1968 with the aim of producing poplar varieties that are climatically suited to, and appropriate for end uses in New Zealand. This variety (or clonal cultivar) originated from this breeding programme from a controlled pollinated cross made in 1985.

This clonal cultivar has been vegetatively propagated (as unrooted 25 cm cuttings) from the original seedling identified by the code NZ 85-069-002. It has subsequently been vegetatively propagated as unrooted cuttings (25 cm), stakes (1 m) and poles (2 m–3 m).

It has been determined from observations of plantings of the above material that the characteristics described herein hold true to form through successive propagations.

SUMMARY OF THE INVENTION

The clonal cultivar was created as a seedling in 1985 from a controlled pollinated cross between a female *P. nigra*

(identified as *P. nigra* 'LP1') and pollen from a male *P. maximowiczii* (itself being an open pollinated seedling, from a known female parent, from Hokkaido Japan and identified as *P. maximowiczii* '73-010-072'.

The cross was carried out at the National Plant Materials Centre, Staces Road, Aokautere, Palmerston North, New Zealand. The resulting seedlings were planted out in nursery beds at the Centre. The first vegetative propagation was from hardwood cuttings of dormant wood, this was also carried out at the National Plant Materials Centre in 1985. Following selections for further trial, cuttings were bulked up and a gene pool planting was established in 1990. Field trial plantings commenced in 1998.

The tree is characterised by good apical dominance resulting in a straight stem, with a steep branch angle giving a narrow crown form. The clonal cultivar shows high resistance to the rusts *Melampsora larici-populina* and *M. medusae* and also to leaf anthracnose *Marssonina brunnea*. It also exhibits low palatability to possums (*Trichosurus vulpecula*).

In a New Zealand context this gives a distinctive variety compared with previous releases by combining narrow crown form with high pest and disease resistance. This clonal cultivar has been named Shinsei.

BOTANICAL DESCRIPTION OF THE VARIETY

Figure 1:
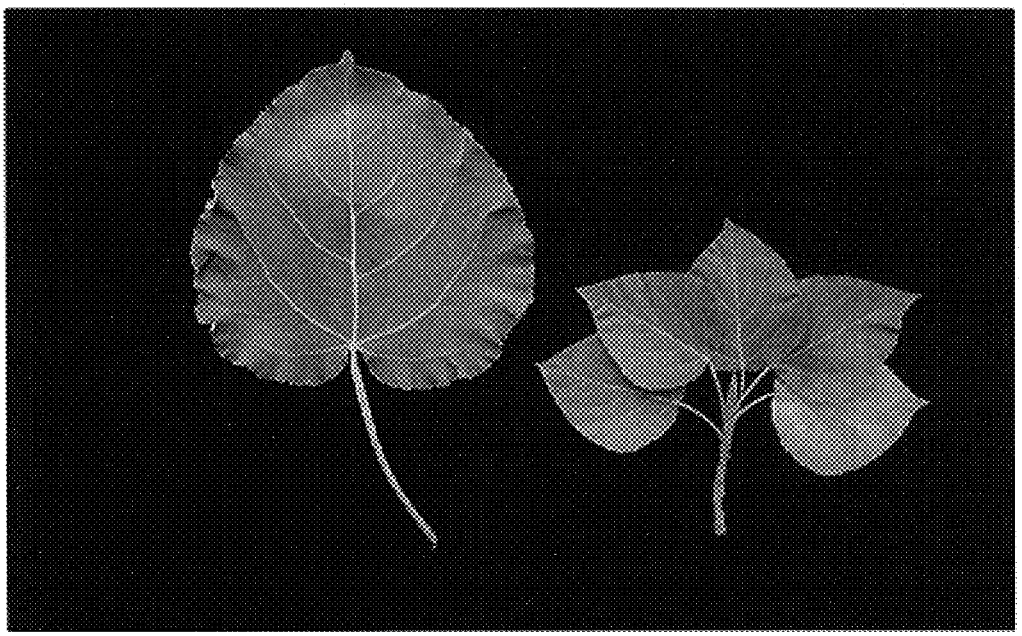
FIG. 1 shows (from left to right) upper surfaces of leaves from: 1) A fully illuminated long branch from a one-year-old cutting and, 2) a fully illuminated short branch from an eleven-year-old tree.
Figure 2:
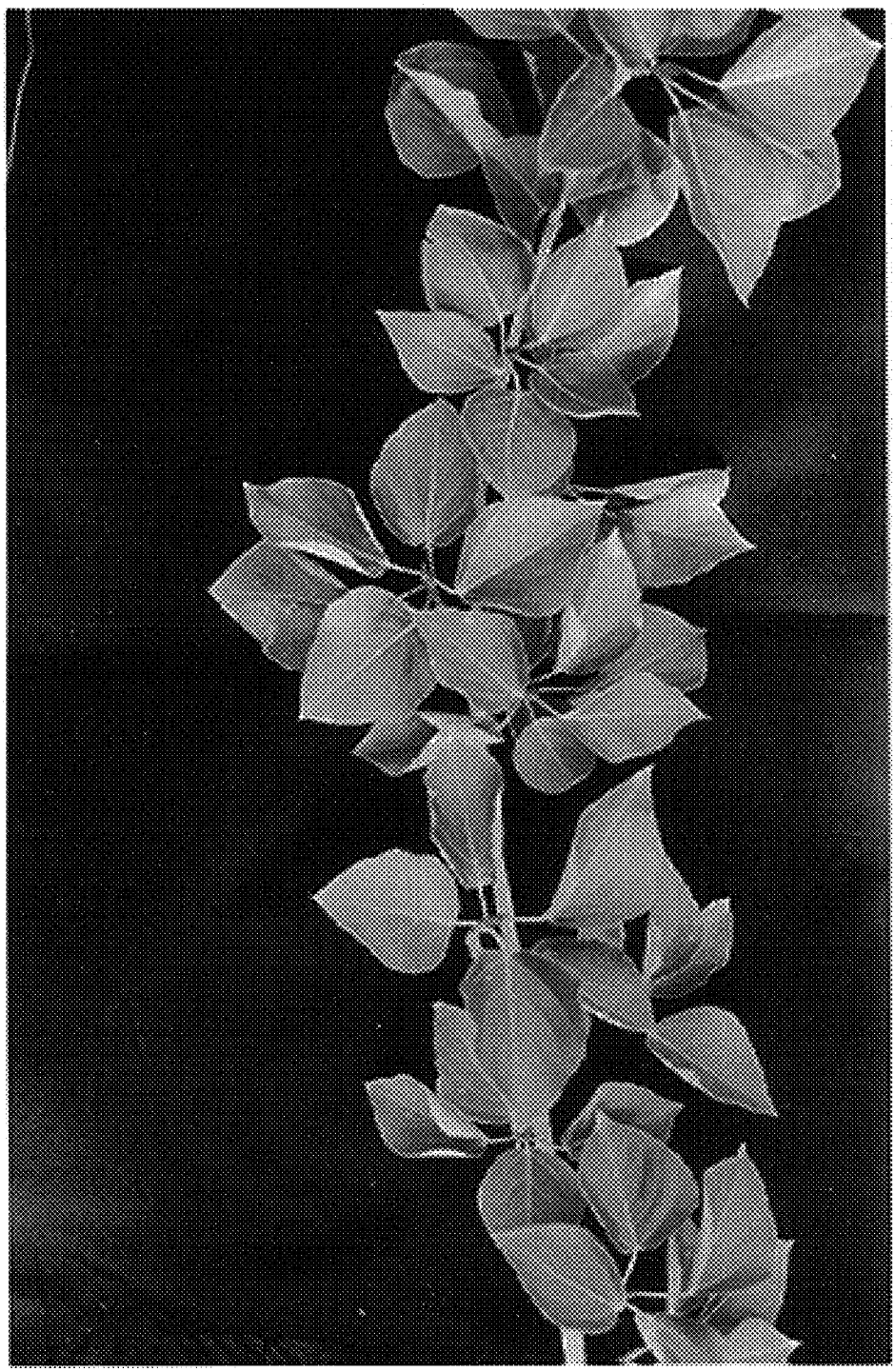
FIG. 2 shows a fully illuminated short branch from an eleven-year-old tree.
Figure 3:
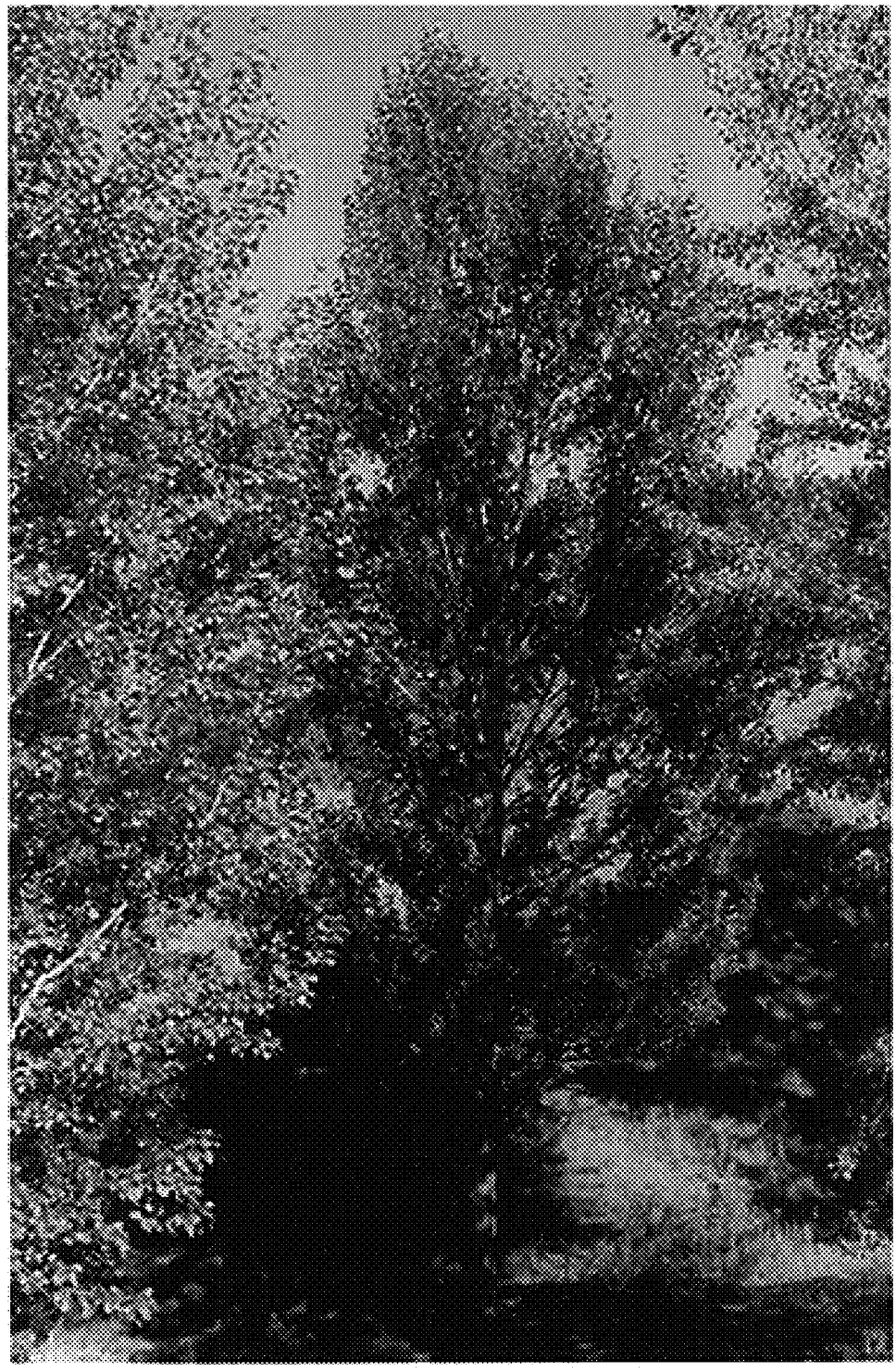
FIG. 3 shows an eleven year-old-tree planted on farmland on a sandy loam and annual rainfall of ca. 1200 mm.
Figure 4:
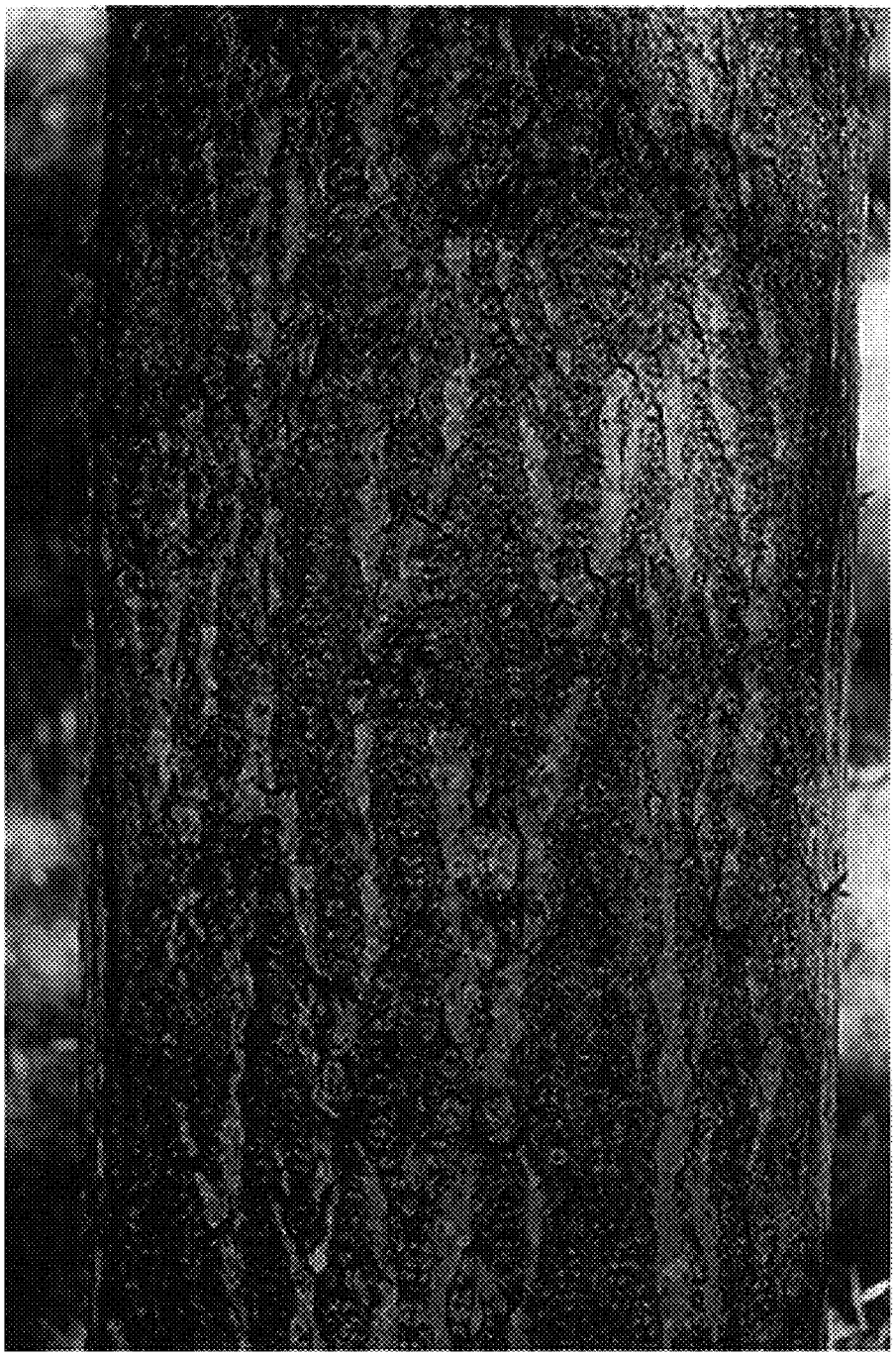
FIG. 4 shows bark from the lower trunk of an eleven-year-old tree.
Figure 5:
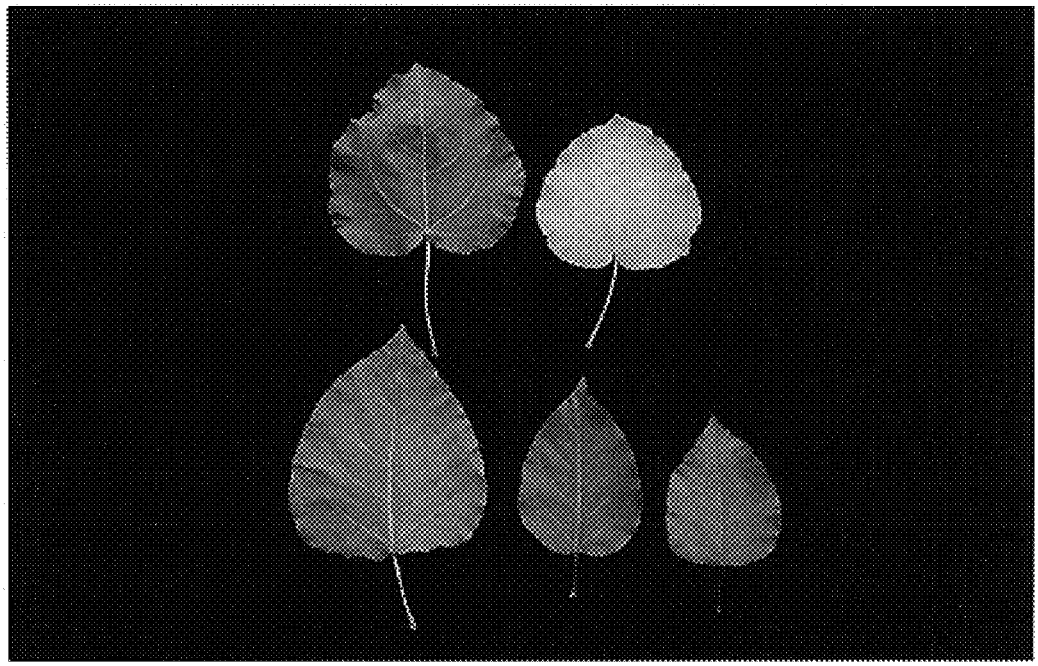
FIG. 5 shows leaves of the clonal cultivar (Shinsei) and its closest varieties (Eridano, Androscoggin, Oxford) from fully illuminated branches of one-year-old cuttings. Top row (from left to right): Upper (adaxial) leaf surface of Shinsei, lower (abaxial) leaf surface of Shinsei. Note moderately cordate base. Bottom row (from left to right): Upper leaf surfaces of Eridano, Androscoggin, Oxford.

The following description are features described as they appear for examples of the variety growing in the province of Manawatu, New Zealand. All dimensions in millimeters, weights in grams (unless otherwise stated). Color chart references are in accord with R.H.S. Color Chart, The Royal Horticultural Society, London (2001 edition).

Young tree

As a young (1–3 years old) tree grown from cuttings in a nursery, the clonal cultivar has a smooth, straight stem form that is circular in cross section at the base and becomes slightly angular at the tip. Trunk diameter typically averages approximately 39 mm in diameter when measured 1400 mm above ground level. Stem color is predominantly grey-green (near Grey-green 197B) at the base, grading to a light green at the tip and lenticels (ranging in shape from round to long linear) are very prominent. Branch angle is acute with the branches tending to curve upwards. Two year old branches (measured at 1400 mm above ground level) typically being at an angle of approximately 70° to 50° to the trunk. The typical average diameter of these branches being approximately 12 mm when measured a short distance (100 mm) from their join with the trunk. Branch and trunk surface is smooth in texture and a similar color (near Greyed-green 197B).

Terminal leaf bud length is typically 20–25 mm and buds are narrow ovate in shape with a narrow acute tip. Color is predominantly green with a red-brown tinge around the bud scale edges. Flower buds are near Greyed-orange 166A in color. The variety is a male clone, and the staminate inflorescence, near Red 42A in color, occurs as a pendulous catkin up to 30 mm in length, with 20–25 stamens.

Leaf color is typically dark-green (near Yellow-green 146A) on the upper (adaxial) surface at maturity and is typically broadly ovate in shape. The base is medium cordate, while the tip is narrow acuminate, and the ratio of the length of the midrib to the width of the leaf is small. Length of petiole relative to that of the midrib varies between half to similar lengths, and the petiole is light green in color and approximately 1.1 to 1.9 mm in diameter. The leaf margin is finely serrate. Hairs are absent from both sides of the leaf and the angle between leaf veins and the midrib are acute. The leaf veins are arranged in a pinnate pattern and are near Green-yellow 1C in color.

Adult tree

Crown width in an open grown situation remains straight and non-spreading and the trunk is similarly straight. Bark on the lower trunk is lightly furrowed at this age and light (near Greyed-green 188D) in color. Branches are typically at an angle of approximately 50° to the trunk.

Mature adult leaf form differs from the juvenile form in that the shape becomes more ovate-rhomboid due to the leaf base becoming slightly cuneiform or rounded cuneiform and the leaf tip more narrow acuminate. Leaf coloration and margin characteristics remain similar to that of the young tree form, as does petiole length relative to midrib length. Vein angle becomes slightly more acute.

Growth Rates

Under nursery conditions height growth from an unrooted 25 cm cutting can be expected to reach 2–3 m in the first growing season and after two years height will be at least 6 m.

Some indicative field trial growth data are as follows:

TABLE 1

| Age | Height (m) | Diameter at 1.4 m (cm) | Planting material |
|---|---|---|---|
| 4 | 7.1–8.2 | 7.1–9.5 | 70 cm unrooted stakes |
| 10 | 16.4 | 24.8 | 3 m unrooted pole |

Comparison to closest variety

A number of hybrids involving male *P. maximowiczii* have been planted in New Zealand, and these would be the closest varieties to this clone:

*P. deltoides*×*P. maximowiczii* 'Eridano'

*P. maximowicziii*×*P. trichocarpa* 'Androscoggin'

*P. maximowicziii*×P.×*berolinensis* 'Oxford'

Major distinguishing features between this clone and those mentioned above are crown width in adult trees and shape of leaf base from long shoots of one-year-old cuttings and can be summarised as follows:

TABLE 2

| Characteristic | Expression of characteristic in Shinsei | Denomination of the closest variety | Expression of characteristic in the named closest variety |
|---|---|---|---|
| Crown width | Straight (narrow) | Eridano | Spreading |
| | | Androscoggin | Spreading |
| | | Oxford | Spreading |
| Shape of leaf base* | Medium cordate | Eridano | Straight |
| | | Androscoggin | Weakly cordate |
| | | Oxford | Straight |

*from long shoots of one-year-old cuttings

Pest and disease resistance

The clonal cultivar shows high resistance to the rusts *Melampsora larici-populina* and *M. medusae* and also to leaf anthracnose *Marssonina brunnea*. It also exhibits low palatability to possums (*Trichosurus vulpecula*).

Plant hardiness

The plant hardiness range (according to the American zone classification) has not been determined. However, under New Zealand conditions, the plants are expected to be winter hardy to −30° C. and have been observed to tolerate temperatures of −6° C. in areas that experience some winter cold and frost, and have also been observed to grow well in conditions where summer heat up to 25° C. is experienced.

We claim:

1. A new and distinct variety (clonal cultivar) of poplar tree, substantially as herein described and illustrated, characterised by a straight, narrow crown form, rapid growth and resistance to *Melampsora larici-populina, M. medusae* (poplar leaf rusts), *Marssonina brunnea* (poplar leaf anthracnose), and low palatability to *Trichosurus vulpecula* (possum).

* * * * *